US00PP23921P3

(12) United States Plant Patent
Beatson

(10) Patent No.: US PP23,921 P3
(45) Date of Patent: Sep. 24, 2013

(54) HOP PLANT NAMED 'HORT7709'

(50) Latin Name: ***Humulus lupulus* L.**
Varietal Denomination: Hort7709

(75) Inventor: Ron Beatson, Motueka (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 13/135,815

(22) Filed: Jul. 15, 2011

(65) Prior Publication Data

US 2013/0019355 P1 Jan. 17, 2013

(51) Int. Cl.
*A01H 5/00* (2006.01)

(52) U.S. Cl.
USPC ..... Plt./236

(58) Field of Classification Search
USPC ..... Plt./236
See application file for complete search history.

*Primary Examiner* — Kent L Bell
(74) *Attorney, Agent, or Firm* — Lathrop & Gage LLP

(57) ABSTRACT

A new and distinct Hop plant is described. The cultivar results out of a selection from a population of seedlings derived from the open pollination of a tetraploid seedling selection 95-28-24 (not patented). The cones are of a small size, oval shape, ripen mid-late season, and have slightly open bracts. The cultivar has been shown to have a unique chemistry profile; of particular interest is the high yield of oil per gram of alpha acid.

4 Drawing Sheets

Genus and species of plant claimed: *Humulus lupulus* L.
Variety denomination: 'Hort7709'.

BACKGROUND TO THE INVENTION

Seed was obtained from open pollination of the unreleased tetraploid seedling selection 95-28-24 (not patented) in the 1996/97 season. 95-28-24 was identified as a tetraploid seedling from the open pollination of 'Liberty' (not patented). Triploid seedlings obtained from this open pollination were grown in a nursery at the Motueka, New Zealand in the 1997/98 season; ploidy level was determined by flow cytometry. The resulting seedlings were then planted out in the field and grown in the 1998/99 season. The seedling, originally designated the breeder code 97-77-09 and later named 'Hort7709', was selected during the 1998/99 season on the basis of its agronomic performance and chemistry profile.

SUMMARY OF THE INVENTION

A new and distinct Hop plant is described. The cones of 'Hort7709' are of a small size, ovate shape, ripen mid-late season, and have slightly open bracts. The cultivar has been shown to have a unique chemistry profile; of particular interest is the high yield of oil per gram of alpha acid.

'Hort7709' was relocated to the seedling selections repository, at the Motueka, New Zealand site, in winter 1999 where it underwent performance monitoring for agronomic and chemistry traits of commercial importance in the 1999/2000 season. During this time it was asexually propagated via rhizome cuttings. 'Hort7709' underwent evaluation in a small plot replicated trial with nine other promising aroma selections for 3 seasons, from 2000/01 to 2002/03.

On the basis of its performance for agronomic, chemistry and brewing characteristics, it was decided to advance 'Hort7709' to large-scale testing. In late winter 2002 a 150-plant plot was established at Motueka, New Zealand and over the next eight seasons the cultivar underwent extensive brewing, agronomic, and chemistry evaluations. In addition to this testing a 500-plant grower trial was established in the Nelson Province in 2005. 'Hort7709' is maintained at Motueka as a 150-plant plot where it has undergone observations for uniformity. All plants have been found to be true to type, that is, no off types have been observed. Under New Zealand growing conditions 'Hort7709' is distinguished from the known parental cultivar 95-28-24 and other cultivars of common knowledge by the following characteristics along with its unique chemistry profile and brewing characteristics.

95-28-24: the maternal parent 95-28-24 is tetraploid whereas 'Hort7709' is triploid, the ploidy level has been confirmed by flow cytometry.

'New Zealand Hallertauer' (not patented): when mature 'Hort7709' vines have an overall club-shape with a medium head volume and a late harvest season, while 'New Zealand Hallertauer' vines are cylindrical in shape with a low head volume and an early harvest season.

'Pacifica' (not patented): when mature 'Hort7709' vines have an overall club-shape, a medium number of thorns, and a reddish-purple stripe, while 'Pacifica' vines are cylindrical in shape, have very few thorns and a green stripe.

BRIEF DESCRIPTION OF THE DRAWINGS

The accompanying photographs show typical specimens of the plant habit, flowers, and leaves of the new cultivar as depicted in colours as nearly true as is reasonably possible to make the same in colour illustrations of this character.

DETAILED DESCRIPTION

Figure 1:
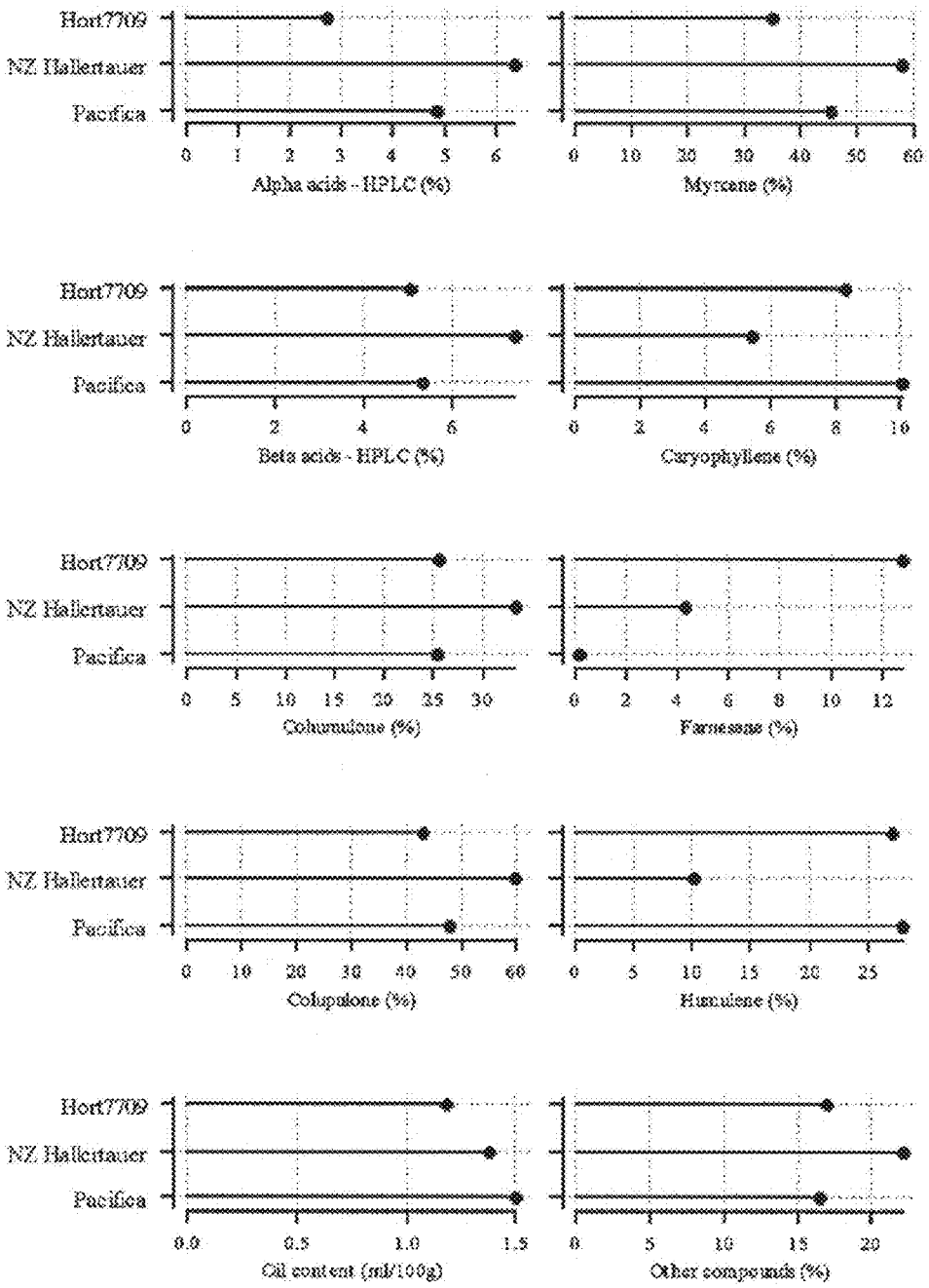
FIG. 1: Five year mean of chemistry profiles for 'Hort7709' at harvest and two comparator cultivars 'New Zealand Hallertauer' (not patented) and 'Pacifica' (not patented). Trials and testing was conducted in Motueka, New Zealand.
Figure 2:
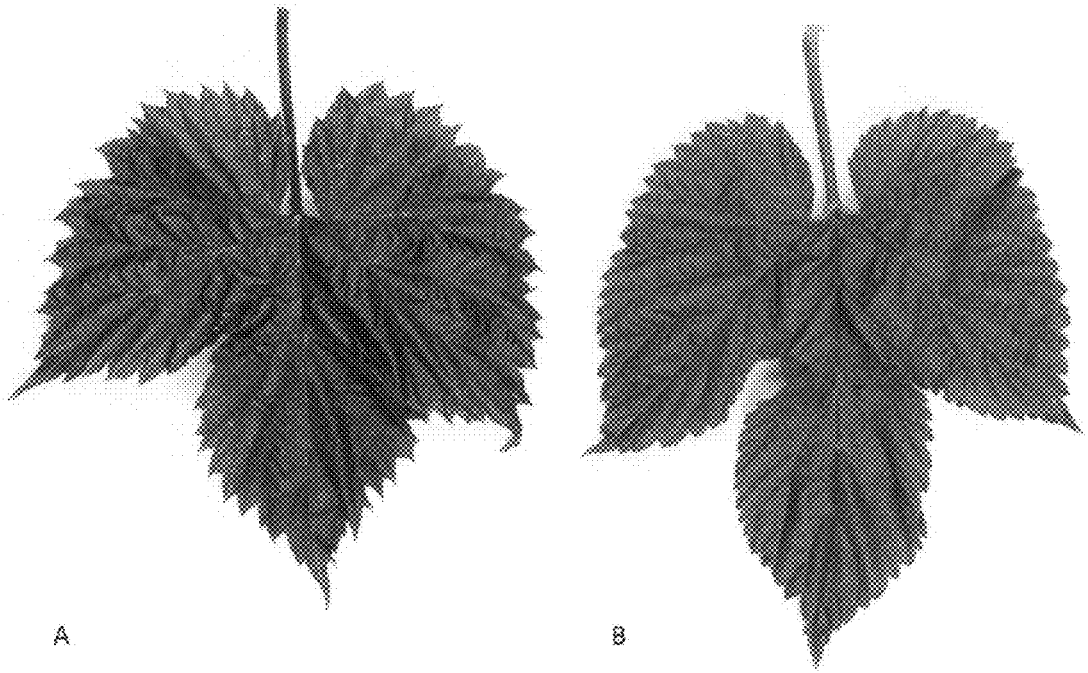
FIG. 2: Mature fully expanded leaves of 'Hort7709' (A) and 'New Zealand Hallertauer' (B).
Figure 3:
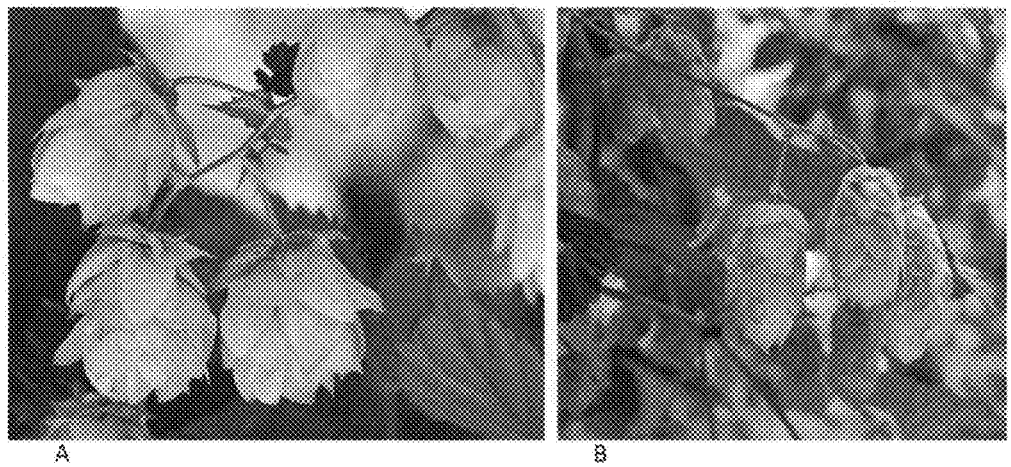
FIG. 3: Cones of 'Hort7709' (A) and 'New Zealand Hallertauer' (B).
Figure 4:
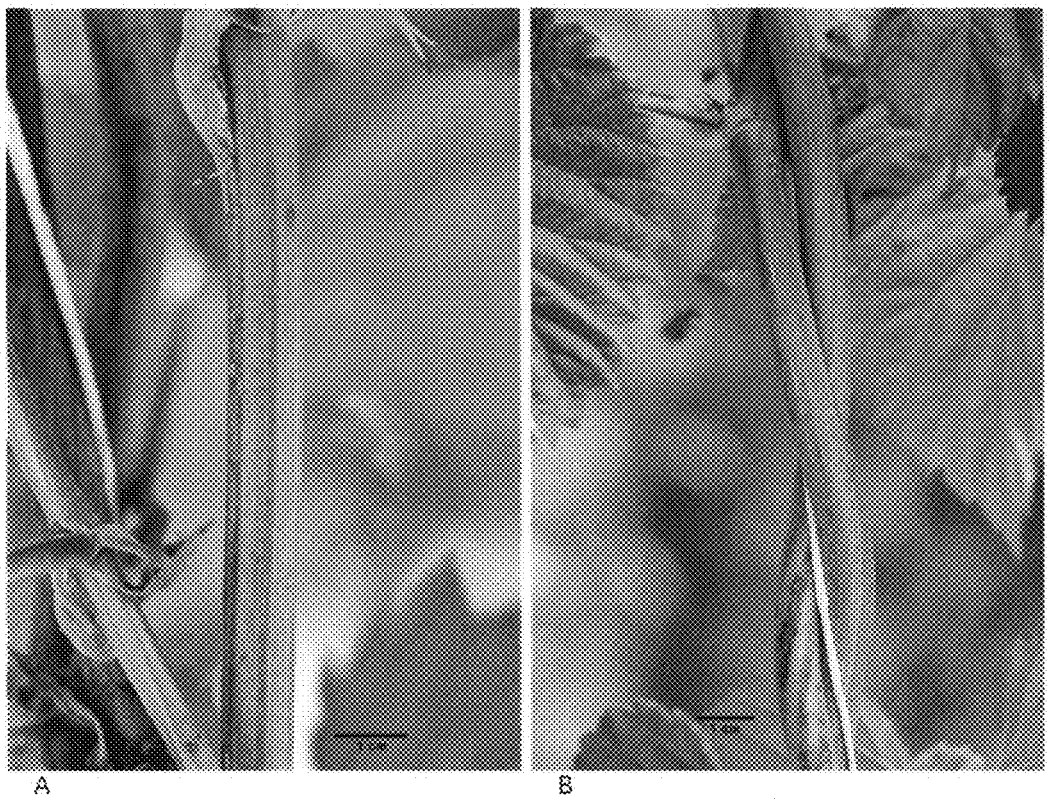
FIG. 4: Close up of mature vines 'Hort7709' (A) and 'New Zealand Hallertauer' (B).

The following is a description of the new cultivar with colour terminology in accordance with The Royal Horticultural Society Colour Charts (R.H.S.C.C.) 2001 edition. The specimens described were grown at Motueka, New Zealand. The observations were made over the 2009-2011 seasons.

Plant form and vigour: Plants are of a normal growth type, are club-shaped when mature and produce a moderate yield (average of approximately 1700 kg/ha). The vine is thick and very vigorous but is relatively slow to establish, training is delayed until later in the season. Hop plants are usually trained in late October-early November in New Zealand, however 'Hort7709' is not ready for training until mid November. The main shoot of the vine, when mature, has a medium number of thorns, an absent or very weak node pubescence, a near greyed purple 187A stripe, background colour of near green 143C with near red purple 59A flecks. One-year-old single strung plants near to harvest maturity had an average main shoot diameter of 10.7 mm with an average internode length of 228 mm.

Laterals: The side shoots from the middle third of the plant were medium in length (an average of approximately 670 mm) and produce a medium number of cones, approximately 13 per node, with an average of 7 nodes per lateral. The upper third of the plant produces longer laterals (an average of 770 mm) and a higher number of cones per lateral, approximately 13 per node, with an average of 11 nodes per lateral. Laterals are predominantly distributed in the top third of the vine, which accounts for the club-shape, in a spreading attitude, and carry an overall medium number of cones.

Leaves: Typical leaf arrangement was opposite. The lamina shape is palmatified, with an average of three strong lobes which ranged from slightly to strongly overlapping, with acuminate apices and slightly imbricate basal lobes. The average length of the lobes was 116.7 mm. The top side of the leaves were coloured between near green 137A and 137B, the underside was between near green 137C and 138A, with veins near yellow green 146C and 146D. The colouration of the veins extended down the underside of the petioles which averaged 68 mm in length and 4.2 mm in width. The rest of the petiole was coloured near greyed purple N186C, this grew slightly lighter towards the leaf end. The margins of the leaves were acutely denate. The topside of the leaves had evenly distributed small white straight trichomes; these were also found along the main veins on the underside of leaves. The petioles had raised lumps the same colour as the surrounding tissue topped with bifid transparent trichomes.

Stipules: Were connate and medium sized with an acute apex which typically splits.

Cone: Were small in size, an average of 39.7 mm long and 25.7 mm in diameter at the widest point, medium ovate in shape and near yellow green 144B and green 143C in colour. The slightly open bracts were an average of 19.9 mm long and 11.6 mm wide at the widest point, with a medium length apex and an acute tip. The cones mature late in the season, $21^{st}$-$30^{th}$ March under average New Zealand conditions.

Chemistry profile: 'Hort7709' has undergone extensive chemistry profile testing and the following are six year data averages (FIG. 1). It is compared with 'Pacifica' and 'New Zealand Hallertauer' as these are commonly grown aroma hop cultivars in New Zealand. The chemistry profile of 'Hort7709' differs significantly from both 'Pacifica' and 'New Zealand Hallertauer' in a number of ways; these include lower content of alpha acids when compared to 'New Zealand Hallertauer' and 'Pacifica', significantly higher percentages of farnesene than either comparator. The proportion of essential oils at harvest found in 'Hort7709' cones differs considerably from that found in either 'Pacifica' or 'New Zealand Hallertauer' as does the overall oil content (mg/100 g). Consequently 'Hort7709' delivers a unique flavour, aroma, and bittering quality when processed and is therefore considered to be distinct. 'Hort7709' has no known particular tolerances or susceptibilities to pests and diseases associated with hop plants.

Use: Flavouring and bittering ingredient for beer in the aroma market.

I claim:

1. A new and distinct hop plant substantially as illustrated and described.

* * * * *

A B